US008939904B2

(12) United States Patent
Lippert et al.

(10) Patent No.: US 8,939,904 B2
(45) Date of Patent: Jan. 27, 2015

(54) MONITORING DEVICE AND METHOD FOR OPERATING A MONITORING DEVICE

(75) Inventors: Michael Lippert, Ansbach (DE); Michael Vollkron, Pressbaum (AT); Gerald Czygan, Buckenhof (DE); Stefan Paule, Drosendorf (DE)

(73) Assignee: Biotronik SE & Co. KG, Berlin (DE)

( * ) Notice: Subject to any disclaimer, the term of this patent is extended or adjusted under 35 U.S.C. 154(b) by 736 days.

(21) Appl. No.: 13/041,025

(22) Filed: Mar. 4, 2011

(65) Prior Publication Data

US 2011/0224748 A1 Sep. 15, 2011

Related U.S. Application Data

(60) Provisional application No. 61/312,685, filed on Mar. 11, 2010.

(51) Int. Cl.
| | |
|---|---|
| *A61B 5/02* | (2006.01) |
| *A61B 5/0205* | (2006.01) |
| *A61B 5/00* | (2006.01) |
| *A61N 1/37* | (2006.01) |
| *A61N 1/365* | (2006.01) |

(52) U.S. Cl.
CPC ........... *A61B 5/0205* (2013.01); *A61B 5/02028* (2013.01); *A61B 5/6846* (2013.01); *A61B 5/7275* (2013.01); *A61N 1/3702* (2013.01); *A61N 1/365* (2013.01)
USPC ....................................................... 600/301

(58) Field of Classification Search
CPC ........ A61B 5/02; A61B 5/0205; A61B 5/021; A61B 5/026
USPC ........................................................ 600/301
See application file for complete search history.

(56) References Cited

U.S. PATENT DOCUMENTS

| | | | | |
|---|---|---|---|---|
| 6,405,085 | B1 * | 6/2002 | Graupner et al. | 607/17 |
| 7,096,064 | B2 * | 8/2006 | Deno et al. | 607/9 |
| 7,330,759 | B2 * | 2/2008 | Militello | 607/17 |
| 7,769,436 | B1 * | 8/2010 | Boileau et al. | 600/509 |
| 8,435,186 | B2 * | 5/2013 | Hettrick et al. | 600/508 |
| 2005/0124900 | A1 | 6/2005 | Stadler et al. | |
| 2005/0240233 | A1 * | 10/2005 | Lippert et al. | 607/6 |
| 2007/0055170 | A1 * | 3/2007 | Lippert et al. | 600/547 |
| 2009/0163969 | A1 | 6/2009 | Donofrio | |
| 2010/0023081 | A1 | 1/2010 | Audet et al. | |
| 2010/0094102 | A1 | 4/2010 | Zhang et al. | |

FOREIGN PATENT DOCUMENTS

EP    2 241 249 A1    10/2010

* cited by examiner

*Primary Examiner* — Christopher D Koharski
*Assistant Examiner* — Jeremiah Kimball
(74) *Attorney, Agent, or Firm* — Muncy, Geissler, Olds & Lowe, P.C.

(57) ABSTRACT

A monitoring device for a patient for predicting a cardiovascular anomaly and a method for operating a monitoring device is provided. Furthermore, an implantable electrotherapy device, such as an implantable cardiac pacemaker, an implantable cardioverter, or an implantable defibrillator, having a monitoring device are also provided. In an embodiment, the monitoring device acquires a value change of a hemodynamic parameter, which occurs as a result of a detected value change of a state parameter, for example, as a result of an activation or deactivation of a cardiac resynchronization therapy. By suitable evaluation of the value change of the hemodynamic parameter, the monitoring device can output an evaluation result signal which is indicative of an imminence of a cardiovascular anomaly, such as a cardiac decompensation, long beforehand and with high specificity.

14 Claims, 2 Drawing Sheets

MONITORING DEVICE AND METHOD FOR OPERATING A MONITORING DEVICE

This nonprovisional application claims priority to U.S. Provisional Application No. 61/312,685, which was filed on Mar. 11, 2010, which is herein incorporated by reference.

BACKGROUND OF THE INVENTION

1. Field of the Invention

The present invention relates to a monitoring device for a patient for predicting a cardiovascular anomaly and a method for operating a monitoring device. Furthermore, the present invention relates to an implantable electrotherapy device, such as an implantable cardiac pacemaker, an implantable cardioverter, or an implantable defibrillator, which is operationally linked to a monitoring device according to the invention.

In particular, the present invention relates to a cardioverter/defibrillator, which is operationally linked to a monitoring device according to the invention for predicting a cardiac decompensation.

2. Description of the Background Art

Monitoring devices and methods for predicting a cardiovascular anomaly are fundamentally known.

For example, in the disclosure of American patent application US 2005/0124900 A1, a method and a device for detecting value changes of physiological parameters and predicting a cardiovascular anomaly based thereon are described. In this method, a value of a physiological parameter, such as a pressure or a heart rate variability, is measured. The measured value is then, on the one hand, averaged over a comparatively long period of time and, on the other hand, averaged over a comparatively short period of time. The value of the physiological parameter averaged over the comparatively long period of time represents a healthy state of the patient. Furthermore, the deviation of the short-term averaged value from the long-term averaged value is recorded and the values of the relative deviation are continuously integrated. An alarm signal indicative of a cardiovascular anomaly is either output if the relative deviation exceeds a first predetermined value or if the integrated relative deviation exceeds a second predetermined value.

SUMMARY OF THE INVENTION

It is therefore an object of the present invention to provide a monitoring device for predicting a cardiovascular anomaly, which is particularly distinguished by the capability of being able to announce a cardiovascular anomaly as long as possible beforehand and with high specificity.

The above-mentioned technical problem is solved according to a first aspect of the present invention for a monitoring device for a patient for predicting a cardiovascular anomaly, which comprises the following components: a first input and a sensor, which is connected to the first input, for acquiring a value of a physiological parameter dependent on a cardiovascular anomaly, the first input and the sensor being implantable; a second input and a detection unit, which is connected to the second input, for detecting a value change of a state parameter different from the physiological parameter, the state parameter being a different physiological parameter or a parameter characterizing a state of a medical device already connected to the patient or another physical or pharmacotherapeutic state of the patient; an analysis unit, which is operationally linked to the implantable sensor and the detection unit, and which is implemented to determine, upon the detection of the value change of the state parameter, a value change of the physiological parameter occurring upon the value change of the state parameter, and to provide a first differential signal as a function of the determined value change of the physiological parameter; a transformation unit, which is implemented to receive the first differential signal and transform it into a characteristic variable as a function of a chronological correlation of the value changes of the state parameter and the physiological parameter and/or as a function of an absolute value and/or a direction of the detected value change of the state parameter and provide it; and/or a prediction unit, which is implemented to receive the characteristic variable and evaluate it and to provide an evaluation result signal indicative of an imminence of a cardiovascular anomaly as a function of the evaluation.

The present invention is based on the finding that known devices for predicting a cardiovascular anomaly, for example, for predicting a cardiac decompensation, a myocardial infarction, a stroke, a worsening of a cardiac insufficiency, or another malfunction of the cardiovascular system, only observe the course of a single physiological parameter. Devices of this type tend to output false alarms, because almost all physiological parameters are also subject to value changes, which are not to be attributed directly to worsening of the cardiovascular system, but rather have other causes. Therefore, the devices of this type have a comparatively low specificity, which is generally disadvantageous.

For example, to predict a cardiovascular anomaly, the delivery rate of the heart can occur on the basis of a value acquisition and analysis of a hemodynamic parameter. The analysis of the curve of a value of such a hemodynamic parameter is made more difficult via the following problems recognized by the inventor, however: worsening of the pumping function of the heart is countered by the body using a plurality of different compensation mechanisms, such as varying the filling pressure, the peripheral resistance, the total quantity of liquid, the heart rate, and the contractility. Because of such variation, the delivery rate of the heart is initially maintained. For example, by increasing the filling pressure of the ventricle, the stroke volume of the heart is initially kept constant. The delivery rate itself only sinks in a late phase, when internal body compensation mechanisms are completely exhausted. Therefore, for example, a cardiovascular anomaly may only be announced relatively late on the basis of an ascertained change of the stroke volume of the heart by solely monitoring the stroke volume. An acceptable specificity in known devices may therefore only be achieved by losses in the advance warning time.

Furthermore, the inventors have recognized that other known devices for predicting a cardiovascular anomaly, which are based on detection of pulmonary edema formation, fundamentally only output an alarm shortly before implementation of clinical symptoms, whereby the advance warning time of these devices is also low. In addition, every worsening of the cardiovascular system does not cause formation of pulmonary edema, which can therefore result in a lack of alarms in monitoring devices which are exclusively based on the detection of pulmonary edema.

The present invention is based on the further finding that to achieve a longer advance warning time, it is expedient to acquire values of one or more physiological parameters, which change comparatively early in the functional chain of a cardiovascular anomaly.

Furthermore and in particular, the inventors have observed that the cardiovascular system reacts differently to a value change of a specific state parameter which causes a disturbance of the cardiovascular system if a cardiovascular anomaly is imminent. This deviating reaction of the cardiovascular system, which is expressed in a change of the strength or the speed of the reaction, for example, is to be attributed to the fact that the possibilities for compensation of the disturbance are already reduced because of the imminence of the cardiovascular anomaly. The deviating reaction may be observed in the heart rate variability (HRV), for example. Expressed in control technology terms, the cardiovascular system may accordingly be described as a control loop, whose control variable reacts differently to a value change of a disturbance variable as a function of imminence of a cardiovascular anomaly.

It is accordingly an idea of the present invention in an embodiment, not to solely continuously record and evaluate a value of a physiological parameter, but rather to determine a value change of the physiological parameter which results because of a value change of a state parameter and to set the value change of the physiological parameter in relation to the value change of the state parameter and thus obtain a characteristic variable, which is used as the basis for a long-term and specific prediction of a cardiovascular anomaly.

On the basis of the evaluation of the characteristic variable, which is composed of the value change of the physiological parameter and alternately the chronological correlation of the value change of the state parameter and the physiological parameter and/or the absolute value and/or the direction of the detected value change of the state parameter, the monitoring device is capable of predicting a cardiovascular anomaly long beforehand, on the one hand, and with a high specificity, on the other hand. Of course, both the patient and also an attending physician directly profit from the long advance warning time.

A further advantage of the monitoring device according to the invention is that long-term changes of the value of the physiological parameter, which are not to be attributed directly to a worsening of the cardiovascular system of the patient, do not result in the output of an alarm in the meaning of an evaluation result signal which announces a cardiovascular anomaly, which further increases the specificity of the monitoring device according to the invention.

Another advantage of the monitoring device according to the invention is that the characteristic variable can be used not only for the purpose of predicting a cardiovascular anomaly, but rather can also be used as the basis for a second analysis, with the aid of which target value changes of the physiological and/or the state parameters may be calculated, which counteract an imminent cardiovascular anomaly. Target value changes of this type may be caused by the monitoring device itself or may be proposed by an attending physician via home monitoring (HM or home monitoring designates a patient remote diagnosis), for example.

The components of the monitoring device are not necessarily all integrated in an implanted housing, but rather may also be situated spatially distributed. The first input and the sensor of the monitoring device are preferably implanted, for example, and the detection unit having the second input is also alternately implanted or situated outside the body of the patient as a function of the type of the state parameter, and the remaining components, namely the analysis unit, the transformation unit, and the prediction unit, are located outside the body of the patient, for example, in a patient device or in a home monitoring center. Accordingly, particular components of the monitoring device are alternately operationally linked to one another via lines and/or wirelessly. The implanted sensor and the detection unit transmit their particular signals via suitable interfaces to the analysis unit, for sample.

As already explained above, the term "cardiovascular anomaly" in the context of the description of the present invention represents an array of cardiovascular malfunctions. These include, for example, cardiac decompensation, a myocardial infarction, a stroke, or acute worsening of the cardiac state, for example, in the context of cardiac insufficiency, by implementation of a heart valve insufficiency, a pericardial tamponade, myocarditis, or significant cardiac rhythm disturbances.

The physiological parameter dependent on such a cardiovascular anomaly is, for example, a hemodynamic parameter, such as a pressure, for example, a pulmonary-arterial pressure (PAP), a right ventricular pressure (RVP), a left ventricular pressure (LVP), an aortic pressure (AoP), a pressure in the left atrium (LAP), a pressure in the right atrium (RAP), a blood pressure, or a bloodflow, a volume, or an acceleration, a biochemical parameter, a contractility, an impedance, or an electrocardiogram. Instead of these physiological parameters, physiological surrogate parameters may alternately be used, which are obtained from a suitable impedance measurement, for example. In the context of the description of the present invention, the term "physiological parameter" also comprises physiological surrogate parameters.

The differential signal provided by the analysis unit as a function of the determined value change of the physiological parameter alternately specifies the determined value change of the physiological parameter itself or a value change derived therefrom of a further physiological parameter, such as the stroke volume (SV), the left or right ventricular end-diastolic volume (LVEDV or RVEDV), the left or right ventricular end-systolic volume (LVESV or RVESV), the left ventricular ejection fraction (LVEF), the time-related left or right ventricular pressure change (RV dP/dtmax or LV dP/dtmax), the left ventricular end-diastolic pressure (LVEDP), the mean or end-diastolic pressure in the left atrium (LAP), the mean or systolic or diastolic aortic pressure (mean/syst/diast AoP), the left ventricular contractility, the pulmonary resistance, a peripheral resistance, a vascular compliance, or corresponding surrogate parameters or a T-wave alternans parameter, such as an ABAB pattern (an alternating repeating pattern), the ST segment elevation, another morphological electrocardiogram parameter, a parameter derived from a pressure-volume diagram, such as the potential energy (PE), the external work (EW), the pressure-volume area (PVA), the effective arterial elasticity (EA), the contractility (Emax), the efficiency of the left or right half of the heart (EW/PE), the so-called pre-load recruitable stroke work (PRSW), or a corresponding surrogate parameter. The determined value change or the derived value changes are preferably chronologically averaged values.

The state parameter is, for example, a parameter characterizing a state of a medical device already connected to the patient, for example, a stimulation parameter, such as a stimulation frequency, an activity of a cardiac resynchronization therapy (CRT on/off), an activity of an antitachycardial stimulation (ATP), an electrode configuration, a pacing mode or a pacing amplitude, a programmed atrioventricular or interventricular delay time, or a stimulation mode.

The state parameter is a different physiological parameter in other embodiments, such as an atrioventricular delay time (AVD), an interventricular delay time (VVD), an intrinsic frequency of the heart, an atrial or ventricular event type, which can be stimulated or intrinsic (i.e., of natural origin), or a parameter characteristic of a presence of an arrhythmia, an atrial flutter (AF), a supraventricular tachycardia (SVT), a ventricular or atrial extrasystole, or another deviating individual heart cycle, such as the first cycles after a defibrillation shock.

The state parameter can also be a parameter characteristic of a physical or pharmacotherapeutic state of the patient, such as a strain which is acquired via a so-called motion sensor, via a minute volume (MV) sensor, or via an activity of a closed loop stimulation (CLS), a respiration frequency or a parameter which is characteristic as to whether the patient is in a sleeping or waking state, whether or not arrhythmias are present, whether the patient is recumbent or standing, whether or not the patient takes medications, such as diuretics, and whether or not there is apnea.

For example, activation or deactivation of a CRT, the rise or fall of the heart rate, a change of the physical position of the patient, taking medications or discontinuing medications, and nervous stimulation, such as a vagal stimulation, represent a value change of the state parameter. Accordingly, an interference of the cardiovascular system typically accompanies the value change of the state parameter or the value change of the state parameter already quantifies a disturbance of the cardiovascular system.

The value change of the state parameter can occur independently or can be provoked for the purposes of monitoring, for example, by the monitoring device itself, this being explained in greater detail hereafter. In the latter case, the monitoring device is not only implemented to detect the value change of the state parameter, but rather to cause it in the first place.

The transformation unit is implemented to transform the first differential signal into a characteristic variable as a function of the chronological correlation of the value changes of the state parameter and the physiological parameter and/or as a function of an absolute value and/or a direction of the detected value change of the state parameter. For example, the transformation unit relates the first differential signal to the duration of the value change of the physiological parameter or to the duration of the value change of the state parameter or to a time duration between the value change of the state parameter and the value change of the physiological parameter. In this embodiment, the characteristic variable accordingly designates a dynamic response of the value change of the physiological parameter as a result of the value change of the state parameter. In another embodiment, the transformation unit relates the first differential signal to an absolute value of the value change of the state parameter and/or to a direction of the value change of the state parameter, whereby the characteristic variable represents a weighted strength or a direction of the value change of the physiological parameter in reaction to the value change of the state parameter or a sensitivity of the physiological parameter with respect to the value change of the state parameter.

The prediction unit is implemented to receive and evaluate the characteristic variable. The evaluation of the characteristic variable is performed, for example, by a comparison of the characteristic variable to already stored comparative values. The stored comparative values may be predefined or may be adaptively determined on the basis of the long-term observed statistical variations of the characteristic variable. The probability for a trend in the sequential values of the characteristic variable can also be determined with the aid of statistical methods, and this trend probability can be compared to a limiting value. To further reduce false alarms, this evaluation can be observed in summary over a time interval of multiple days to weeks.

Further exemplary embodiments of the monitoring device according to the invention are described hereafter. Additional features of the further exemplary embodiments may be combined with one another and with optional features already described above to form other embodiments, if these features are not explicitly described as alternative to one another.

In an embodiment, the analysis unit of the monitoring device is implemented to determine the value change of the state parameter and to provide a second differential signal as a function of the specific value change of the state parameter. In this embodiment, the transformation unit is implemented to provide a quotient of the first differential signal and the second differential signal as the characteristic variable.

The second differential signal either specifies the determined value change of the state parameter itself or a value change derived therefrom. For example, the transformation unit transforms the first differential signal into the characteristic variable according to equation 1:

$$\text{characteristic variable} = \frac{\Delta(\text{physiological parameter})}{\Delta(\text{state parameter})} \quad (1)$$

whereby $\Delta$ (physiological parameter) designates the value change of the physiological parameter and $\Delta$ (state parameter) designates the value change of the state parameter.

In this embodiment, characteristic variable accordingly represents a sensitivity of the physiological parameter with respect to a value change of the state parameter. This embodiment suggests itself in particular if the state parameter is a different physiological parameter, such as the heart rate, the strain, the breathing rate, or the atrioventricular delay time (AVD).

In particular in the above-mentioned embodiment, the analysis unit can be implemented for the purpose of continuously recording the value of the physiological parameter and chronologically averaging it for a short time and storing the short-term average value of the physiological parameter and continuously updating it and determining the value change of the physiological parameter as the difference between a current acquired value of the physiological parameter and the previously stored value of the physiological parameter, i.e., the value of the physiological parameter stored chronologically before the value change of the state parameter.

The analysis unit can be implemented for the purpose of performing averaging of the value of the physiological parameter in determined predefined value ranges, which are also designated as bins hereafter, of the state parameter, for example, in the case of a heart rate as the state parameter, in the value ranges: 40-60 bpm (beats per minute); 60-80 bpm; 80-100 bpm; 100-120 bpm.

This is advantageous in particular if a natural variation of a state parameter is observed, whose variation range is not fixed, e.g., the heart rate. The acquired values of the physiological parameter are averaged separately in the various ranges of the state parameter. This data set can be analyzed at regular intervals (e.g., every 24 hours). The first differential signal is only then calculated in the form of the value change of the physiological parameter between various state ranges, i.e., the difference of bin mean values, and can also be related to the associated value changes of the state parameter (e.g., state parameter difference between the state ranges, bin interval). This allows the averaging of acquired values without being able to check the state parameter or knowing its variation range.

For example, the analysis unit determines the value change of the physiological parameter from the stored bin mean values of the physiological parameter for value ranges of the state parameter according to one of the following methods: calculating the width of the value range covered by the bin mean values of the physiological parameter; calculating a mean value from mean value differences between adjacent bins, upon varying bin spacing, each standardized to the bin interval; calculating a mean value, which is standardized to the bin interval, of all paired differences between all bins and weighting this mean value with the number of the acquisition actions; or calculating a slope of an ascertained fit curve of the bin mean values of the physiological parameter, plotted against the state parameter.

A variation of the heart rate can occur independently because of a natural sinusoidal frequency or can be caused intentionally by frequency adaptation using an implant, for example. A variation of an atrioventricular delay time as an alternative state parameter can also arise independently because of the intrinsic atrioventricular delay time or can be caused intentionally by a programmed atrioventricular dynamic response or by automatic atrioventricular tracking.

In another embodiment, the transformation unit of the monitoring device can be implemented to additionally transform the differential signal into the characteristic variable as a function of an external condition, such as "rest state" or "movement state", and the prediction unit is also implemented to evaluate the characteristic variable as a function of the external conditions, such as "rest state of the patient" or "movement state of the patient". For example, the analysis unit of the monitoring device only records values of the physiological parameter if a specific external condition is fulfilled, such as "rest state of the patient".

The monitoring device achieves a further increase of the specificity by this separate observation of the acquired values of the state parameter and the physiological parameter.

In a further embodiment of the monitoring device, the analysis unit can be implemented to ascertain a time duration between the beginning of the value change of the state parameter and the end of the value change of the physiological parameter. In this embodiment, the transformation unit is implemented to relate the first differential signal to the ascertained time duration and to provide the time-related first differential as the characteristic variable. Alternatively, the transformation unit provides the ascertained time duration itself as the characteristic variable.

In this embodiment, the characteristic variable accordingly describes a dynamic response of a reaction in the form of the value change of the physiological parameter occurring upon the value change of the state parameter. This embodiment is particularly advantageous if the value change of the state parameter occurs suddenly, as is the case, for example, upon occurrence of an extrasystole or an appearance of atrial flutter.

In an embodiment, the monitoring device can comprise additional implantable first component for causing an intentional value change of the state parameter. The monitoring device is accordingly implemented to provoke the value change of the physiological parameter by intentional value change of the state parameter. The state parameter is preferably a parameter characterizing a state of a medical device already connected to the patient, such as a cardiac pacemaker, a cardioverter, a defibrillator, or a CRT device, in this embodiment.

Accordingly, the monitoring device can comprise, for example, an implantable first component for varying a stimulation frequency, a component for varying the atrioventricular or interventricular delay time, a component for varying the stimulation mode, or a component for activating and deactivating a cardiac resynchronization therapy. In this embodiment, the transformation unit can transform the first differential signal as a function of the chronological correlation of the value changes of the state parameter and the physiological parameter.

Before the background of the finding that the cardiovascular system of the patient reacts differently to specific disturbances if a cardiovascular anomaly, such as a cardiac decompensation, is imminent, the cardiovascular system of the patient is intentionally disturbed by the monitoring device by causing an intentional value change of the state parameter and the reaction is acquired in the form of the value change of the physiological parameter and transformed by the transformation unit as a function of the chronological correlation of the value changes of the state parameter and the physiological parameter into a characteristic variable and is evaluated by the prediction unit. In this way, the monitoring device is capable of providing and outputting the evaluation signal, which is indicative for the imminence of a cardiovascular anomaly, very long beforehand and with high specificity.

In an embodiment, the monitoring device repeatedly causes, for example, every 60 minutes, for a short time, for example, lasting a few cardiac cycles or for a few minutes, a specific, preferably sudden value change of the state parameter and acquires a value of the physiological parameter before, during, and after the value change of the state parameter.

The analysis unit can be implemented in this embodiment of the monitoring device to provide the first differential signal as the mean value of a plurality of determined value changes of the physiological parameter, which occur upon a plurality of detected value changes of the state parameter. In this way, value changes of the physiological parameter which are to be attributed to reasons other than the value change of the state parameter are hardly reflected in the first differential signal, whereby the specificity of the monitoring device is finally increased further.

The transformation unit can be also implemented to chronologically average the characteristic variable over a specific period of time, for example, over 24 hours, and to provide this chronologically average characteristic value to the prediction unit for evaluation. The influence on the value change of the physiological parameter of causes other than the value change of the state parameter is reduced by the chronological averaging and the specificity of the monitoring device is thus increased further.

The absolute value of the intentional value change of the state parameter can be, for example, predefined or can be established adaptively by the monitoring device as a function of the determined value change of the physiological parameter.

The characteristic variable is, for example, a difference of a value of the physiological parameter, standardized to the value change of the state parameter, immediately before the value change of the state parameter from a value of the physiological parameter at an established end of the value change of the state parameter.

In another embodiment, the characteristic variable can be descriptive for a dynamic response of the reaction in the form of the value change of the physiological parameter occurring upon the value change of the state parameter. In this embodiment, the transformation unit preferably transforms the first differential signal into the characteristic variable as a function of the chronological correlation of the value changes of the state parameter and the physiological parameter. For example, the transformation unit sets the first differential signal, for example, in the form of the value change of the physiological parameter itself, in relation to a reaction time, which is defined as the half-life period or as the relaxation time of a decaying exponential function, for example, or in relation to an initial value change speed of the physiological parameter, i.e., in relation to an initial slope of the value of the physiological parameter. On the other hand, the reaction time, the half-life period, the relaxation time, or the initial slope can itself be the characteristic variable.

Other examples of the characteristic variable are, for example, an initial value change speed, which is standardized to the value change of the state parameter, of the physiological parameter, the level of an overshoot beyond a final equilibrium state, or the level of the overshoot beyond the final equilibrium state, which is standardized to the value change of the state parameter.

In another embodiment of the monitoring device, the implantable first component solely cause a single short-term value change of the state parameter, for example, a brief elevation of the stimulation frequency or cause an artificial "extrasystole", e.g., by a premature stimulation. In this embodiment, the characteristic variable is the strength and direction in relation to the value change of the state parameter of the value change of the physiological parameter caused by the value change of the state parameter, such as a heart rate jump in the event of an intentionally caused extrasystole. Other examples of the characteristic variable in this embodiment of the monitoring device are the determined value change of the physiological parameter in relation to a reaction time defined as the half-life period or relaxation time of a decaying exponential function or in relation to an initial value change speed of the physiological parameter or the initial value change speed standardized to an amplitude and duration of the value change of the state parameter, the level of a first overshoot, the level of the first overshoot standardized to the amplitude and duration of the value change of the state parameter, the level of a second overshoot, or the level of the second overshoot standardized to the amplitude and duration of the value change of the state parameter. On the other hand, the amplitude and duration of the value change of the physiological parameter, the reaction time, the half-life time, the relaxation time, the initial slope, the level of the first overshoot, or the level of the second overshoot itself can be the characteristic variable.

Using intentionally caused value changes of the state parameter, which only last a few cardiac cycles, the monitoring device checks comparatively rapid compensation mechanisms of the patient, such as the Frank Starling effect, the Bowditch effect, or autonomous regulation, while the monitoring device checks regulatory compensation capabilities of the entire cardiovascular system of the patient using those intentionally caused value changes of the state parameter which last several minutes to several hours.

In an embodiment of the monitoring device, the implantable sensor is implemented to acquire a value of a hemodynamic parameter as the physiological parameter, preferably a hemodynamic parameter which changes early in the functional chain of a cardiac decompensation. The detection unit of the monitoring device is preferably implemented to detect a change of a stimulation mode of a medical device already connected to the patient as the value change of a state parameter.

In an embodiment of the monitoring device, the detection unit acquires the natural (intrinsic or frequency-adapted) heart rate as the state parameter. A surrogate parameter derived from a suitable impedance measurement is used as the physiological parameter for the stroke volume or the end-systolic volume. The analysis unit averages values of the physiological parameter in a vector of bins for predetermined heart rate intervals, such as 40-60, 60-80, 80-100, 100-120, 120-140, 140-180 bpm, and evaluates the physiological parameters every 24 hours. The characteristic variable is the mean difference of all adjacent heart rate bins. The transformation unit calculates the characteristic variable by a statistical analysis of the trend probability. The prediction unit compares the characteristic variable to a limiting value. Alternately, instead of the impedance surrogate parameter for the stroke volume or the end-systolic volume, the pulmonary-arterial pressure measured using a pressure sensor implanted in the pulmonary artery can be used (as a surrogate parameter for the left ventricular end-diastolic pressure); or a stroke volume can be obtained by pulse contour analysis from the pulmonary-arterial pressure.

In another embodiment, the implantable first component of the monitoring device repeatedly cause an artificial elevation of the stimulation frequency as the state parameter by a determined value, for example, by 10 bpm above the normal value for 60 cardiac cycles once per hour. This provocation of the heart rate elevation only occurs at low cardiac frequencies, for example, 40-90 bpm, and during rest (no motion signal) of the patient. A surrogate parameter derived from a suitable impedance measurement is used as the physiological parameter for the stroke volume or the end-systolic volume. The analysis unit determines the first different show signal, for example, the value change of the stroke volume or the value change of the end-systolic volume, immediately after every provocation and averages them over a longer period of time, such as 24 hours. The characteristic variable is the mean value change of the physiological parameter. The prediction unit evaluates the characteristic variable by comparison to the statistical variation width averaged over the long time. Alternately, instead of the impedance surrogate parameter for the stroke volume or the end-systolic volume, the pulmonary-arterial pressure measured using a pressure sensor implanted in the pulmonary artery can be used (as a surrogate parameter for the left ventricular end-diastolic pressure); or a stroke volume can be obtained by pulse contour analysis from the pulmonary-arterial pressure.

In a further preferred embodiment of the monitoring device, the transformation unit is implemented to transform the first differential signal into a plurality of characteristic variables as a function of the chronological correlation of the value changes of the state parameter and the physiological parameter and/or as a function of the absolute value and/or the direction of the detected value change of the state parameter and to provide this plurality. Furthermore, in this embodiment the prediction unit is implemented to receive and evaluate the plurality of characteristic variables and, as a function of the plurality of the valuations, to provide an evaluation result signal which is indicative of the imminence of a cardiovascular anomaly.

In this embodiment, a part of the plurality of characteristic variables is preferably descriptive of a sensitivity of a reaction in the form of the value change of the physiological parameter occurring upon a value change of the state parameter and another part of the plurality of characteristic variables is descriptive of a dynamic response of this reaction. The monitoring device has a further improved specificity and longer advance warning time by the evaluation of the plurality of characteristic variables using the prediction unit.

In a further embodiment, the prediction unit is further implemented to determine a target value change of the state parameter from the characteristic variable, an actual value change of the state parameter according to the determined target value change counteracting an imminent cardiovascular anomaly.

The implantable first component of the monitoring device are preferably implemented to cause an actual value change of the state parameter according to the determined target value change. In this embodiment, the state parameter is an atrioventricular delay time, for example. The monitoring device initially causes a value change of the atrioventricular delay time, to thus acquire a value change of a hemodynamic parameter and finally to generate the characteristic variable. From the characteristic variable, the prediction unit determines the target value change of the state parameter which would counteract a cardiovascular anomaly, for example, a determined lengthening of the atrioventricular delay time. The implantable first component then cause a corresponding variation of the atrioventricular delay time, for example.

A second aspect of the present invention is formed by an implantable electrotherapy device, which is operationally linked to a monitoring device according to the invention and comprises second component for outputting an electrical therapy signal. The implantable electrotherapy device shares the advantages of the monitoring device according to the invention of the first aspect of the invention.

The implantable electrotherapy device is preferably implemented to output the electrical therapy signal as a function of the evaluation result signal of the monitoring device.

The implantable electrotherapy device is, for example, a cardiac pacemaker, a cardioverter, a defibrillator, or a combined cardioverter/defibrillator.

In an embodiment, the implantable electrotherapy device is a CRT implant, which is connected to a monitoring device according to the invention, having automatic AVD/VVD adaptation. The automatic AVD/VVD adaptation varies the AV time and/or the VV time at regular intervals, so that after a determined time, all permitted combinations of AVD and VVD values are acquired. This mechanism is used in addition to the monitoring of the patient. The combination of AVD and VVD is used as the state parameter. A surrogate parameter, which is derived from a suitable impedance measurement, for the stroke volume or the end-systolic volume is used as the physiological parameter. The analysis unit of the monitoring device of the CRT implant averages values of the physiological parameter in a matrix of bins for all possible AVD/VVD combinations and evaluates them regularly, for example, every 24 hours. The characteristic variable is the width of the covered area of the value of the physiological parameter stored in the matrix. The characteristic variable is calculated by the analysis unit by a statistical analysis of the trend probability and compared to a limiting value by the prediction unit.

A third aspect of the invention is formed by a method for operating a monitoring device, which comprises the following steps: acquiring a value of a physiological parameter dependent on a cardiovascular anomaly; detecting a value change of a state parameter different from the physiological parameter, the state parameter being a different physiological parameter or a parameter characterizing a state of a medical device already connected to the patient or a parameter characterizing another physical or pharmacotherapeutic state of the patient; upon the detection of the value change of the state parameter: determining a value change of the physiological parameter occurring upon the value change of the state parameter and providing a first differential signal as a function of the acquired value change of the physiological parameter; transforming the differential signal into a characteristic variable as a function of a chronological correlation of the value changes of the state parameter and the physiological parameter and/or as a function of an absolute value and/or a direction of the detected value change of the state parameter and providing the characteristic variable; evaluating the characteristic variable and providing an evaluation result signal, which is indicative of an imminence of a cardiovascular anomaly, as a function of the evaluation.

The method for operating a monitoring device of the third aspect of the invention shares the advantages of the monitoring device of the first aspect of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

It is to be noted beforehand that the geometrical configuration of the components of the monitoring device or the electrotherapy device shown in the figures has no specific relationship to an actual construction of the monitoring device or the electrotherapy device.

The components of the monitoring device particularly do not all have to be integrated in a housing, but rather may be situated spatially distributed. For example, the first input and the sensor of the monitoring device are preferably implanted, the detection unit having the second input is alternately also implanted or situated outside the body of the patient as a function of the type of the state parameter, and the remaining components, namely the analysis unit, the transformation unit, and the prediction unit, are located outside the body of the patient, for example, in a patient device or in a home monitoring center. The implanted sensor and the detection unit transmit their particular signals via suitable interfaces to the analysis unit.

Figure 1:
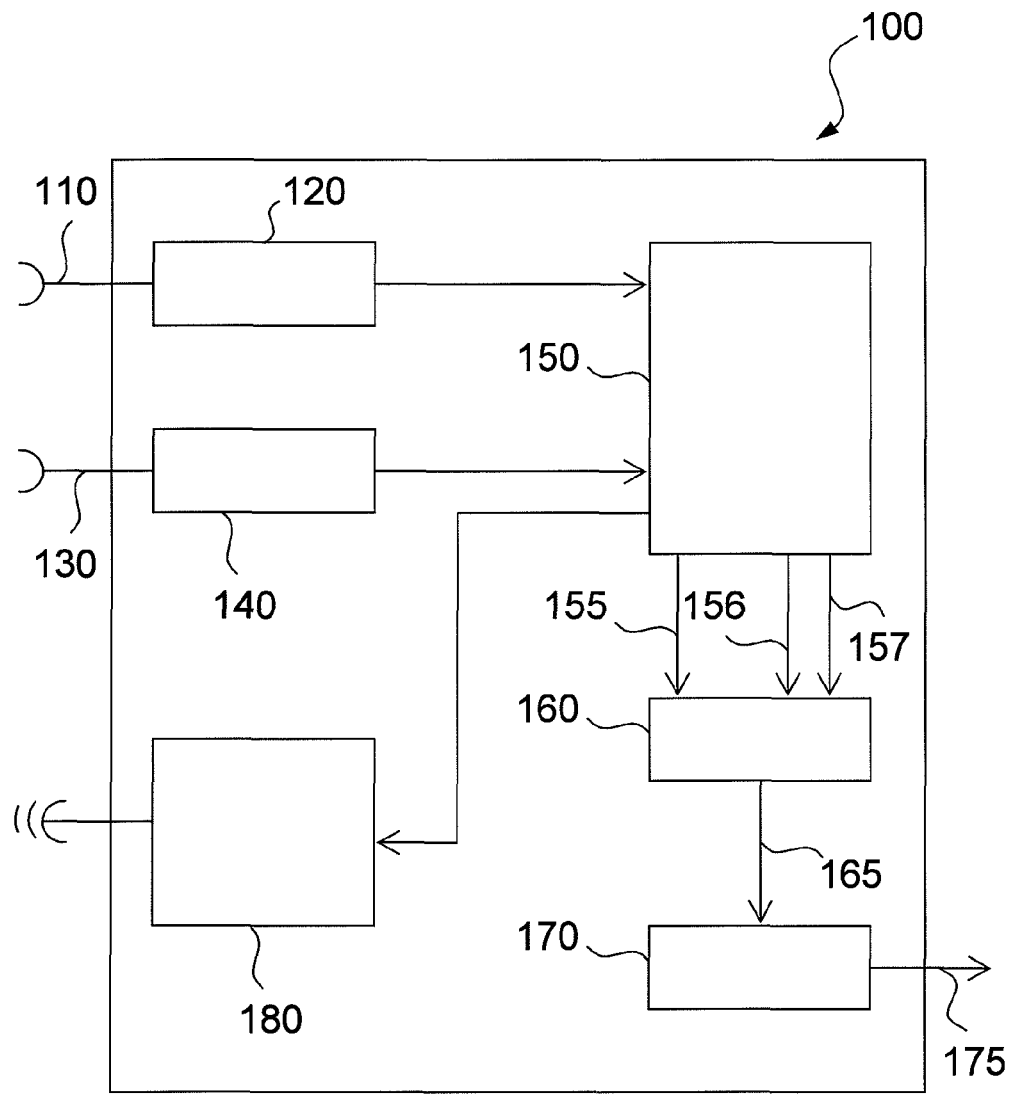
FIG. 1: shows an embodiment of the monitoring device of the first aspect of the invention.

FIG. 1 shows a schematic illustration of a preferred embodiment (100) of the monitoring device according to the invention for a patient for predicting a cardiovascular anomaly. The monitoring device 100 comprises a first input 110 and a sensor 120, connected to the first input 110, for acquiring a value of a physiological parameter dependent on a cardiovascular anomaly. The first input 110 and the sensor 120 are implantable. The monitoring device 100 further comprises a second input 130 and a detection unit 140, connected to the second input 130, for detecting a value change of a state parameter different from the physiological parameter. The detection unit 140 and the second input 130 are alternately implanted or located outside the patient.

Therefore, the frame shown in FIG. 1 around a plurality of components of the monitoring device 100 does not represent an implant housing, for example, but rather is primarily used to illustrate that all components shown in FIG. 1 are part of this embodiment of the monitoring device 100.

As a function of the determined value change of the physiological parameter and the detected value change of the state parameter, the monitoring device 100 provides an evaluation result signal 175, which is indicative of an imminence of a cardiovascular anomaly.

An analysis unit 150 is operationally linked to the implantable sensor 120 and the detection unit 140, which is implemented, upon the detection of the value change of the state parameter, to determine a value change of the physiological parameter occurring upon the value change of the state parameter and to provide a first differential signal 155 as a function of the determined value change of the physiological parameter. The first differential signal 155 accordingly characterizes the value change of the physiological parameter, which typically occurs in reaction to a value change of the state parameter. As already explained above, the analysis unit 150 can be located outside the patient, for example, in a patient device or in a home monitoring center. In this case, the analysis unit 150 preferably receives the particular signals wirelessly.

A transformation unit 160 receives the first differential signal 155 and transforms the first differential signal 155 into a characteristic variable 165, alternately as a function of a chronological correlation of the value changes of the state parameter and the physiological parameter and/or as a function of an absolute value and/or a direction of the detected value change of the state parameter. Through the transformation of the first differential signal 155 into the characteristic variable 165, the value change of the physiological parameter is accordingly set in relation, using the transformation unit, to a time curve of the value changes of the state parameter and the physiological parameter, whereby the characteristic variable 165 would describe a dynamic response of the reaction, or is set in relation to the value change of the state parameter itself, whereby the characteristic variable 165 would be characteristic of a sensitivity of the reaction.

The monitoring device 100 further comprises a prediction unit 170, which is implemented to receive and evaluate this characteristic variable 165 and to provide and output an evaluation result signal 175, which is indicative of an imminence of a cardiovascular anomaly, as a function of the evaluation. The evaluation is performed by comparison to already stored comparative values, for example.

As explained above, the transformation unit 160 and the prediction unit may be located outside the patient, for example, in a patient device or in a home monitoring center.

The evaluation result signal 175 is received, for example, by a further electrotherapy device (not shown in greater detail in FIG. 1), which is implemented to perform a therapy of the patient as a function of this evaluation result signal 175.

In the embodiment of the monitoring device 100 shown in FIG. 1, the analysis unit 150 is additionally implemented to determine the value change of the state parameter and to provide a second differential signal 156 as a function of the determined value change of the state parameter. In this embodiment, the state parameter is a heart rate of the patient or an atrioventricular delay time, for example. The transformation unit 160 also receives the second differential signal 156 and provides the characteristic variable 165 as the quotient of the first differential signal 155 and the second differential signal 156 in one embodiment.

The analysis unit 150 is alternatively or additionally implemented for the purpose of ascertaining a time duration between the beginning of the value change of the state parameter and the end of the value change of the physiological parameter and to provide it to the transformation unit 160 as the ascertained time duration 157. The transformation unit 160 is implemented to relate the first differential signal 155 alternately to the second differential signal 156 and/or to the ascertained time duration 157 and to output it as the characteristic variable 165. The characteristic variable can also be identical to the ascertained time duration 157, however.

The monitoring device 100 further comprises implantable first component 180, which are operationally linked to the analysis unit 150, for causing an intentional value change of the state parameter. As already explained at another point of the description, the present invention is based on the finding that the cardiovascular system of the patient reacts differently to a disturbance if a cardiovascular anomaly, such as a cardiac decompensation, is imminent. In this meaning, the monitoring device 100 provokes targeted disturbances of the cardiovascular system of the patient in the form of intentionally caused value changes of a state parameter using the implantable first component 180. For example, the monitoring device 100 is thus implemented to change the stimulation frequency of a cardiac pacemaker of the patient or to activate or deactivate a cardiac resynchronization therapy or to manipulate the atrioventricular delay time via the implantable first component 180. The detection unit 140 detects such a value change of the state parameter. The value change of the physiological parameter, such as a hemodynamic parameter, occurring upon the value change of the state parameter is acquired and determined by the implantable sensor 120 and by the analysis unit 150.

Figure 2:
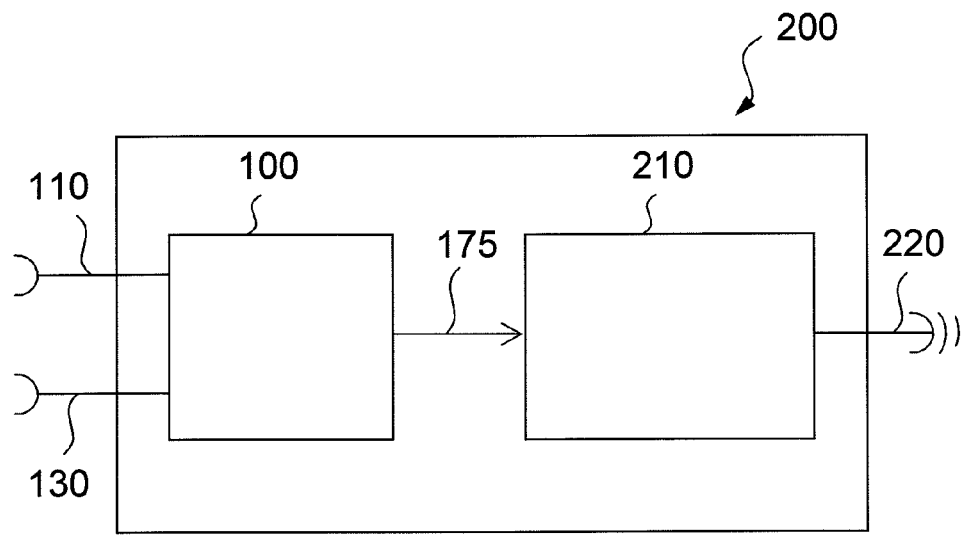
FIG. 2: shows an embodiment of the implantable electrotherapy device of the second aspect of the invention.

FIG. 2 shows a preferred embodiment of the implantable electrotherapy device according to the invention. The implantable electrotherapy device 200 is operationally linked to a monitoring device 100 according to the invention, comprising a first input 110 for acquiring a value of a physiological parameter and a second input 130 for detecting a value change of a state parameter. As described for FIG. 1, the monitoring device 100 generates an evaluation result signal 175 as a function of the acquired value change of the physiological parameter and, for example, the acquired value change of the state parameter with the aid of an analysis unit, a transformation unit, and a prediction unit. Furthermore, the implantable electrotherapy device 200 comprises second component 210 for outputting an electrical therapy signal 220. The therapy signal 220 is a stimulation pulse, for example. The second component 210 are preferably implemented to output the electrical therapy signal as a function of the evaluation result signal 175.

The implantable electrotherapy device 200 is a cardiac pacemaker, an implantable cardioverter, or an implantable defibrillator, for example.

Figure 3:
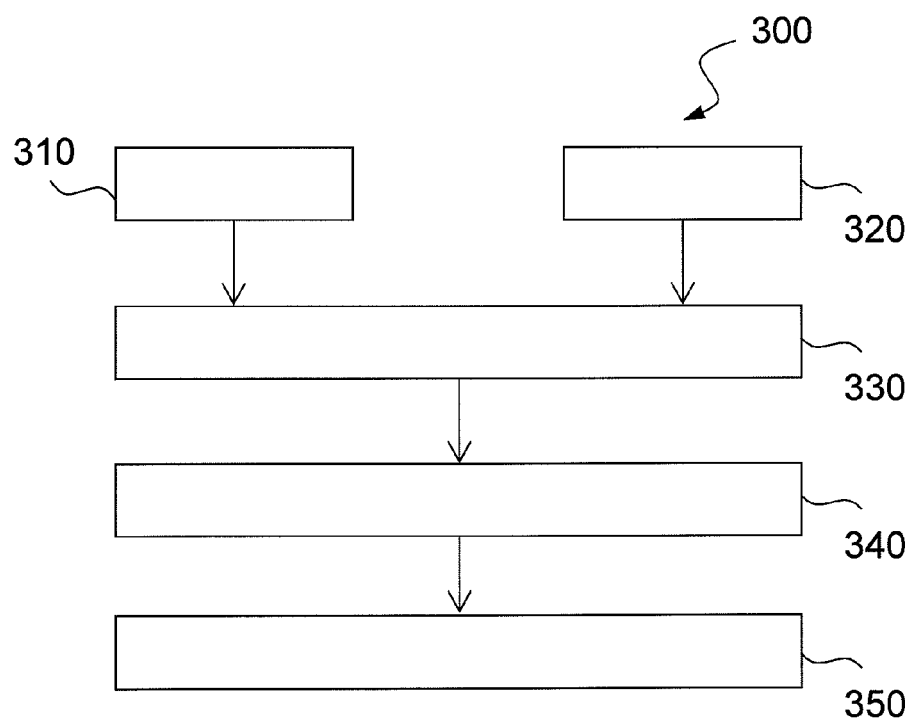
FIG. 3: shows a flowchart of an embodiment of the method for operating a monitoring device according to the third aspect of the invention.

FIG. 3 shows a schematic view of a flowchart of a preferred embodiment of the method according to the invention for operating a monitoring device according to the third aspect of the present invention. According to this method 300, a value of a physiological parameter dependent on a cardiovascular anomaly is acquired continuously in a first step 310.

In a second step 320, a value change of a state parameter different from the physiological parameter is detected.

Upon the detection of the value change of the state parameter, in a third step 330, a value change of the physiological parameter occurring upon the value change of the state parameter is determined and a first differential signal is provided as a function of the acquired value change of the physiological parameter.

In a fourth step 340, the differential signal is transformed into a characteristic variable as a function of a chronological correlation of the value change of the state parameter and the physiological parameter and/or as a function of an absolute value and/or a direction of the detected value change of the state parameter and the characteristic variable is provided.

Finally, in a fifth step 350, this characteristic variable is evaluated and an evaluation result signal indicative of an imminence of a cardiovascular anomaly is provided as a function of the evaluation.

The present invention relates to a monitoring device for a patient for predicting a cardiovascular anomaly and a method for operating a monitoring device. Furthermore, the present invention relates to an implantable electrotherapy device, such as an implantable cardiac pacemaker, an implantable cardioverter, or an implantable defibrillator, having a monitoring device according to the invention. In one embodiment, the monitoring device according to the invention acquires a value change of a hemodynamic parameter, which occurs as a result of a detected value change of a state parameter, for example, as a result of an activation or deactivation of a cardiac resynchronization therapy. By suitable evaluation of the value change of the hemodynamic parameter, the monitoring device can output an evaluation result signal indicative of an imminence of a cardiovascular anomaly, such as a cardiac decompensation, long beforehand and with high specificity.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A monitoring device for a patient for predicting a cardiovascular anomaly, the monitoring device comprising:
   a first input;
   a sensor connectable to the first input and configured to acquire a value of a physiological parameter based on a cardiovascular anomaly, the first input and the sensor being implantable;
   a second input;
   a detection unit connectable to the second input and configured to detect a value change of a state parameter that is different from the physiological parameter, the state parameter being a different physiological parameter or a parameter characterizing a state of a medical device connected to the patient or a parameter characterizing another physical or pharmacotherapeutic state of the patient;
   an analysis unit operationally linked to the implantable sensor and the detection unit, the analysis unit configured to, upon a detection of the value change of the state parameter, determine a value change of the physiological parameter occurring upon the value change of the state parameter and configured to provide a first differential signal as a function of the determined value change of the physiological parameter;
   a transformation unit configured to receive the first differential signal and to transform it into a characteristic variable as a function of a chronological correlation of the value changes of the state parameter and the physiological parameter and/or as a function of an absolute value and/or a direction of the detected value change of the state parameter and to provide it; and
   a prediction unit configured to receive and evaluate the characteristic variable and to provide an evaluation result signal indicative of an imminence of a cardiovascular anomaly as a function of the evaluation, wherein the analysis unit is configured to ascertain a time duration between the beginning of the value change of the state parameter and the end of the value change of the physiological parameter and wherein the transformation unit is configured to relate the first differential signal to the ascertained time duration and to provide the time-related first differential signal as the characteristic variable.

2. The monitoring device according to claim 1, wherein the analysis unit is configured to continuously record the value of the physiological parameter and to chronologically average it for a short time and to store the short-term average value of the physiological parameter and continuously update it and to determine the value change of the physiological parameter as the difference between a currently acquired value of the physiological parameter and the previously stored value of the physiological parameter.

3. The monitoring device according to claim 1, further comprising an implantable first component configured to cause an intentional value change of the state parameter.

4. The monitoring device according to claim 3, wherein the implantable sensor and the analysis unit for determining the value change of the physiological parameter are configured to acquire a value of the physiological parameter before, during, and after the intentional value change of the state parameter.

5. The monitoring device according to claim 4, wherein the analysis unit is configured to provide the first differential signal as a mean value of a plurality of determined value changes of the physiological parameter, which occur upon a plurality of detected value changes of the state parameter.

6. The monitoring device according to claim 1, wherein the implantable sensor is configured to acquire a value of a hemodynamic parameter as the physiological parameter.

7. The monitoring device according to claim 1, wherein the detection unit is configured to detect a change of a stimulation mode of a medical device connected to the patient as a value change of a state parameter.

8. The monitoring device according to claim 1, wherein the transformation unit is configured to transform the first differential signal into a plurality of characteristic variables as a function of the chronological correlation of the value changes of the state parameter and the physiological parameter and/or as a function of the absolute value and/or the direction of the detected value change of the state parameter and to provide this plurality, and wherein the prediction unit is configured to receive and evaluate the plurality of characteristic variables and to provide an evaluation result signal indicative of an imminence of a cardiovascular anomaly as a function of the plurality of evaluations.

9. The monitoring device according to claim 1, wherein the transformation unit is configured to average the characteristic variable and to provide the chronologically averaged characteristic variable to the prediction unit for evaluation.

10. An implantable electrotherapy device, which is operationally linked to a monitoring device according to claim 1 and comprises a second component for outputting an electrical therapy signal.

11. A cardiac pacemaker, which is operationally linked to a monitoring device according to claim 1.

12. An implantable cardioverter or implantable defibrillator, which is operationally linked to a monitoring device according to claim 1.

13. The monitoring device according to claim 1, wherein the transformation unit is located downstream of the analysis unit.

14. A method for operating a monitoring device, the method comprising:

acquiring a value of a physiological parameter based on a cardiovascular anomaly;

detecting a value change of a state parameter that is different from the physiological parameter, the state parameter being a different physiological parameter or a parameter characterizing a state of a medical device connected to the patient or a parameter characterizing another physical or pharmacotherapeutic state of the patient;

determining, upon the detection of the value change of the state parameter, a value change of the physiological parameter occurring upon the value change of the state parameter;

providing a first differential signal as a function of the acquired value change of the physiological parameter;

transforming the differential signal into a characteristic variable as a function of a chronological correlation of the value changes of the state parameter and the physiological parameter and/or as a function of an absolute value and/or a direction of the detected value change of the state parameter and providing the characteristic variable; and evaluating the characteristic variable and providing an evaluation result signal, which is indicative of an imminence of a cardiovascular anomaly, as a function of the evaluation, wherein a time duration is ascertained between the beginning of the value change of the state parameter and the end of the value change of the physiological parameter and wherein the first differential signal is related to the ascertained time duration and the time-related first differential signal is provided as the characteristic variable.

* * * * *